US012678094B1

(12) United States Patent
Naamad et al.

(10) Patent No.: US 12,678,094 B1
(45) Date of Patent: Jul. 14, 2026

(54) DETERMINING SLEEP-RELATED BREATHING EVENTS USING SENSOR DATA FROM A WEARABLE DEVICE

(71) Applicant: Amazon Technologies, Inc., Seattle, WA (US)

(72) Inventors: Yonatan Naamad, Sunnyvale, CA (US); Nina Mishra, Pleasanton, CA (US)

(73) Assignee: Amazon Technologies, Inc., Seattle, WA (US)

( * ) Notice: Subject to any disclaimer, the term of this patent is extended or adjusted under 35 U.S.C. 154(b) by 652 days.

(21) Appl. No.: 18/064,656

(22) Filed: Dec. 12, 2022

(51) Int. Cl.
A61B 5/00 (2006.01)
A61B 5/0205 (2006.01)
A61B 5/145 (2006.01)

(52) U.S. Cl.
CPC .......... *A61B 5/4818* (2013.01); *A61B 5/0205* (2013.01); *A61B 5/14542* (2013.01); *A61B 5/7282* (2013.01); *A61B 2560/0431* (2013.01)

(58) Field of Classification Search
CPC . A61B 5/4818; A61B 5/0205; A61B 5/14542; A61B 5/7282; A61B 2560/0431
See application file for complete search history.

(56) References Cited

U.S. PATENT DOCUMENTS

2019/0175026 A1* 6/2019 Verzal ................... A61B 5/4848

FOREIGN PATENT DOCUMENTS

| CN | 104207755 A | * | 12/2014 | |
|----|----|----|----|----|
| WO | WO-2021152526 A1 | * | 8/2021 | .......... A61M 16/161 |
| WO | WO-2021220202 A1 | * | 11/2021 | ............. A61B 5/168 |
| WO | WO-2022046939 A1 | * | 3/2022 | .......... A61B 5/4818 |

OTHER PUBLICATIONS

Abeyratne, U. R. et al. "Pitch Jump Probability Measures for the Analysis of Snoring Sounds in Apnea," Abstract Only, Physiological Measurement, 26(5):779-798, 2005, three pages of abstract.
Al-Angari, Haitham M. and Alan V. Sahakian. "Automated Recognition of Obstructive Sleep Apnea Syndrome Using Support Vector Machine Classifier," IEEE Transactions on Information Technology in Biomedicine, 16(3):463-468, 2012, URL: https://www.ncbi.nlm.nih.gov/pmc/articles/PMC4487628/.
Alvarez, D. et al. "A Machine Learning-Based Test for Adult Sleep Apnoea Screening at Home Using Oximetry and Airflow," Scientific Reports, 10(1):1-12, 2020.

(Continued)

*Primary Examiner* — Eric F Winakur
*Assistant Examiner* — Sienna C Pyle
(74) *Attorney, Agent, or Firm* — Athorus, PLLC

(57) ABSTRACT

Described are systems and methods for detecting sleep-related breathing events during a sleep session of a user based on sensor data from a wearable device, such as a wrist-worn wearable device. For example, disclosed implementations detect biometric changes of the user that may be indicative of sleep-related breathing events and determine, based on features determined from those biometric changes, that a sleep-related breathing event has occurred. In addition, the disclosed implementations provide a presentation and explanation of the determined sleep-related breathing events.

20 Claims, 8 Drawing Sheets

(56) References Cited

OTHER PUBLICATIONS

Barnes, L. D. et al. "Detection of Sleep Apnea From Single-Channel Electroencephalogram (EEG) Using an Explainable Convolutional Neural Network," bioRxiv, 2021, Accessed Jan. 11, 2023, URL: https://www.researchgate.net/publication/350825200_Detection_of_sleep_apnea_from_single-channel_electroencephalogram_EEG_using_an_explainable_convolutional_neural_network, 31 pages.

Bsoul, M. et al. "Apnea MedAssist: Real-Time Sleep Apnea Monitor Using Single-Lead ECG," IEEE Transactions on Information Technology in Biomedicine, 15(3):416-427, 2010.

Chen, L. et al. "An Automatic Screening Approach for Obstructive Sleep Apnea Diagnosis Based on Single-Lead Electrocardiogram," IEEE Transactions on Automation Science and Engineering, 12(1):106-115, 2014, URL: https://www.researchgate.net/publication/273170776_An_Automatic_Screening_Approach_for_Obstructive_Sleep_Apnea_Diagnosis_Based_on_Single-Lead_Electrocardiogram.

Chen, Lili and Xi Zhang. "State-Based General Gamma CUSUM for Modeling Heart Rate Variability Using Electrocardiogramagnals," IEEE Transactions on Automation Science and Engineering, 14(2):1160-1171, 2015.

Fleming, W. E. et al. "Use of Blood Biomarkers to Screen for Obstructive Sleep Apnea," Nature and Science of Sleep, 10:159-167, 2018, URL: https://www.ncbi.nlm.nih.gov/pmc/articles/PMC6005302/.

Jiménez-García, J. et al. "Assessment of Airflow and Oximetry Signals to Detect Pediatric Sleep Apnea-Hypopnea Syndrome Using AdaBoost," Entropy, 22(6):670, 2020, URL: https://www.researchgate.net/publication/342232221_Assessment_of_Airflow_and_Oximetry_Signals_to_Detect_Pediatric_Sleep_Apnea-Hypopnea_Syndrome_Using_AdaBoost, 20 pages.

Juang, C-F. et al. "Explainable Fuzzy Neural Network with Easy-To-Obtain Physiological Features for Screening Obstructive Sleep Apnea-Hypopnea Syndrome," Sleep Medicine, 85:280-290, 2021.

Khandoker, A. H. et al. "Support Vector Machines for Automated Recognition of Obstructive Sleep Apnea Syndrome from ECG Recordings," IEEE transactions on Information Technology in Biomedicine, 13(1):37-48, 2009, URL: https://www.researchgate.net/publication/23763856_Support_Vector_Machines_for_Automated_Recognition_of_Obstructive_Sleep_Apnea_Syndrome_From_ECG_Recordings.

Kirszenblat, R. et al. "Validation of the Withings ScanWatch as a Wrist-Worn Reflective Pulse Oximeter: Prospective Interventional Clinical Study," Journal of Medical Internet Research, 23(4):e27503, 2021, URL: https://www.researchgate.net/publication/350812552_Validation_of_Withings_ScanWatch_as_a_Wrist-Worn_Reflective_Pulse_Oximeter_Hypoxia_Study_Preprint, 12 pages.

Koley, Bijoy Laxmi and Debangshu Dey. "On-Line Detection of Apnea/Hypopnea Events Using SpO2 Signal: A Rule-Based Approach Employing Binary Classifier Models," IEEE Journal of Biomedical and Health Informatics, 18(1):231-239, 2013.

Mendez, M. O. et al. "Automatic Screening of Obstructive Sleep Apnea from the ECG Based on Empirical Mode Decomposition and Wavelet Analysis," Physiological Measurement, 31(3):273-289, 2010, URL: https://www.esat.kuleuven.be/sista/docs/0967-3334_31_3_001.pdf.

Mendez, M. O. et al. "Sleep Apnea Screening by Autoregressive Models from a Single ECG Lead," IEEE Transactions on Biomedical Engineering, 56(12):2838-2850, 2009 URL: https://www.researchgate.net/publication/224584500_Sleep_Apnea_Screening_by_Autoregressive_Models_From_a_Single_ECG_Lead.

Mendonca, F. et al. "A Review of Obstructive Sleep Apnea Detection Approaches," IEEE Journal of Biomedical and Health Informatics, 23(2):825-837, 2018, URL: https://drive.google.com/file/d/1vUhHBnRBlecnGKbRIH5efkpXIz5TeyHI/view.

Nakano, H. et al. "Tracheal Sound Analysis Using a Deep Neural Network to Detect Sleep Apnea," Journal of Clinical Sleep Medicine, 15(8):1125-1133, 2019, URL: https://jcsm.aasm.org/doi/pdf/10.5664/jcsm.7804.

Nikkonen, S. et al. "Artificial Neural Network Analysis of the Oxygen Saturation Signal Enables Accurate Diagnostics of Sleep Apnea," Scientific Reports, 9(1):1-9, 2019, URL: https://www.researchgate.net/publication/335802652_Artificial_neural_network_analysis_of_the_oxygen_saturation_signal_enables_accurate_diagnostics_of_sleep_apnea.

Penzel, Thomas and AbdelKebir Sabil. "The Use of Tracheal Sounds for the Diagnosis of Sleep Apnoea," Breathe, 13(2):e37-e45, 2017, URL: https://breathe.ersjournals.com/content/breathe/13/2/e37.full.pdf.

Ragette, R. et al. "Diagnostic Performance of Single Airflow Channel Recording (ApneaLink) in Home Diagnosis Of Sleep Apnea," Abstract Only, Sleep and Breathing, 14(2):109-114, 2010, one page abstract.

Selvaraj, Nandakumar and Ravi Narasimhan. "Detection of Sleep Apnea on a Per-Second Basis Using Respiratory Signals," In 2013 35th Annual International Conference of the IEEE Engineering in Medicine and Biology Society (EMBC), pp. 2124-2127. IEEE, 2013, URL: https://vitalconnect.com/wp-content/uploads/2017/02/Selvaraj2013EMBC_OSAeventDetectionRespiratorySignals.pdf.

Ye, G. et al. FENet: A Frequency Extraction Network for Obstructive Sleep Apnea Detection. IEEE Journal of Biomedical and Health Informatics, 25(8):2848-2856, 2021, URL: https://repository.kaust.edu.sa/bitstream/handle/10754/666882/jbhi[1].pdf?sequence=1.

* cited by examiner

DETERMINING SLEEP-RELATED BREATHING EVENTS USING SENSOR DATA FROM A WEARABLE DEVICE

BACKGROUND

Wearable devices are increasing in popularity. Many of the current devices include sensors that are operable to measure a variety of metrics about the user wearing the device. Metrics include heart rate, blood pressure, motion, step count, sleep quality, sleep state, etc. However, sleep-related breathing disorders, such as apnea and hypopnea, require sensor data from sensors that are not available on a wearable device, such as sensors that measure airflow.

BRIEF DESCRIPTION OF DRAWINGS

The detailed description is described with reference to the accompanying figures.

DETAILED DESCRIPTION

Described are systems and methods for detecting sleep-related breathing events during a sleep session of a user based on sensor data from a wearable device, such as a wrist-worn wearable device. As described further below, disclosed implementations detect biometric changes of the user that may be indicative of sleep-related breathing events and determine, based on features determined from those biometric changes, that a sleep-related breathing event has occurred. In addition, the disclosed implementations provide a presentation and explanation of the determined sleep-related breathing events.

Apnea and hypopnea are two common sleep disorders that cause users to repeatedly pause (apnea) or reduce (hypopnea) their breathing during a sleep session, thereby impacting sleep quality and overall health. This may be due to physiological problems (e.g. the tongue blocking the airway of the user), neurological complications, etc. It is estimated that over twenty-two million Americans suffer from sleep apnea, with eighteen million of these cases being undiagnosed. Apnea has been shown to adversely affect memory, mood, attentiveness, cardiovascular function, weight, and has possible connections to diabetes risks, liver function, asthma, and acid reflux.

Typically, apnea incidence and severity are measured using the capital Apnea-Hypopnea Index ("AHI"), which is defined as the average number of apnea or hypopnea episodes experienced per hour of sleep during a sleep session. AHI may be used to rank the severity of a user's apnea on a scale from "normal" (0-5 events per hour), to "mild" (5-15 events per hour), to "moderate" (15-30 events per hour), to "severe" (30+ events per hour). Apnea and Hypopnea are typically diagnosed in laboratory sleep studies, in which a sleep clinician interprets the readings of a large number of sensors (collectively called a polysomnogram) in order to compute the user's AHI. Such clinical studies are known to be costly, inconsistent, slow; and subject to both known and undetectable prejudices. Accordingly, there is a technical improvement to the detection of sleep-related breathing events without the need for expensive equipment or laboratory studies.

The disclosed implementations utilize sensor data from a wearable device to detect sleep-related breathing events, as well as provide explanatory details as to how each second of a time series during a user's sleep session contributed to an AHI score, and how each feature value determined for features contributed to the determination of the AHI score.

Figure 1:
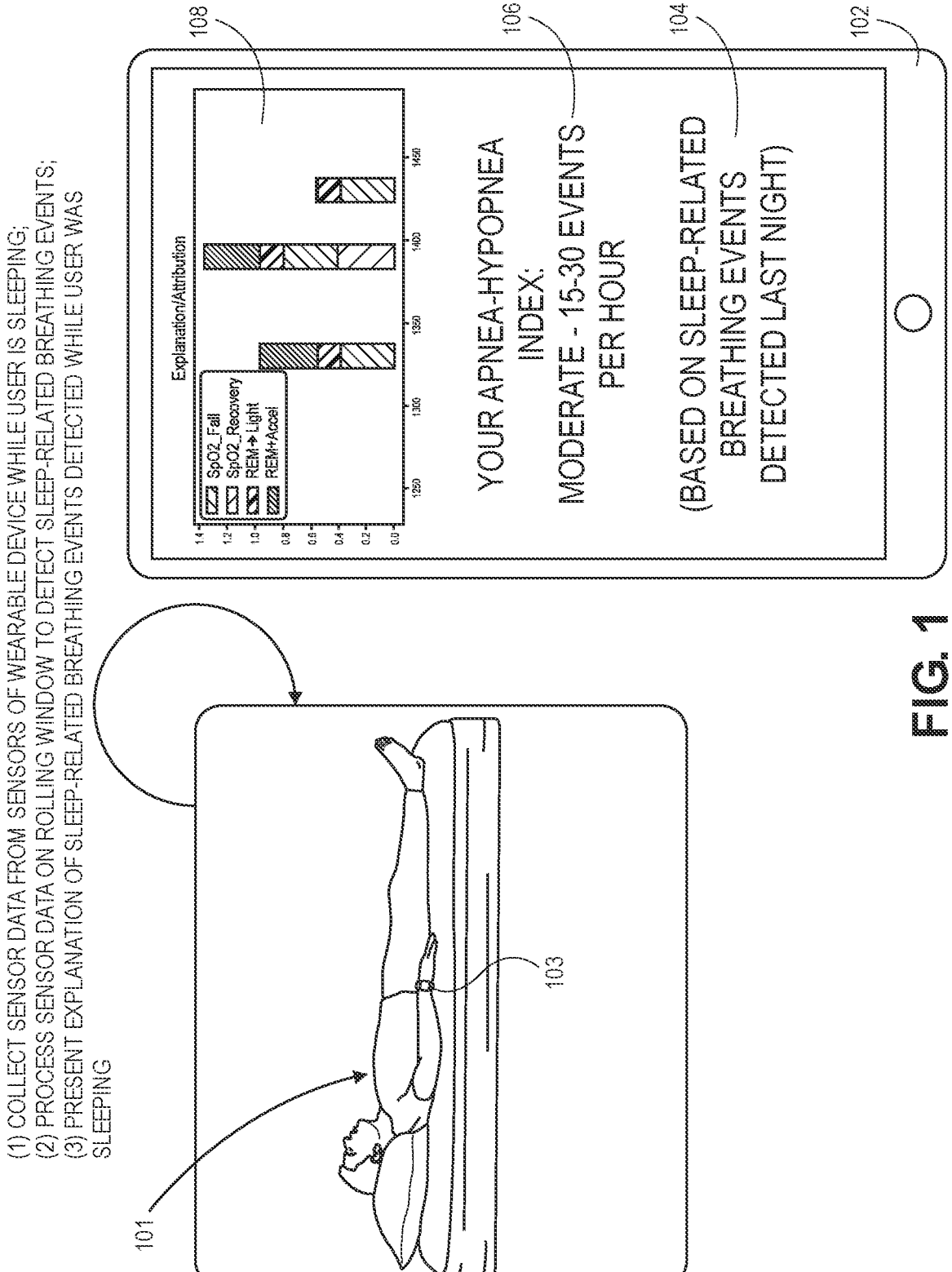
FIG. 1 is a transition diagram illustrating the collection of sensor data from a wearable device, determination of sleep-related breathing events from the sensor data, and presentation of detected sleep-related breathing events, in accordance with described implementations.

FIG. 1 is a transition diagram illustrating the collection of sensor data, determination of sleep-related breathing events from the sensor data, and presentation of detected sleep-related breathing events, in accordance with described implementations.

During a sleep session of a user 101, sensor data is collected by one or more sensors of a wearable device 103 worn by the user 101 during the sleep session. A wearable device may be any type of device that is worn, attached to, laid on, laid upon, or otherwise associated with the user during a sleep session and that includes one or more sensors that may generate time-series sensor data related to the user. For example, but not as a way of limitation, the wearable device may be a wrist band, arm band, neck band, head band, ring, necklace, clothing, etc. Alternatively, the wearable device may be included in material the user lay's upon or that is laid upon by the user during a sleep session, such as a sheet, a pillow, a blanket, a comforter, a mattress, box springs, bed frame, etc. Accordingly, the time-series data that is discussed herein may be time-series sensor data collected from multiple wearable devices during a user sleep session. Likewise, sensor data may be collected from a plurality of sensors of one or more wearable devices. Sensors may include, but are not limited to, an SpO2 sensor, a heart rate sensor, an accelerometer or other motion sensor, a temperature sensor, a transducer (such as a microphone), etc.

While the user 101 is sleeping, time-series data is collected from sensors of the wearable device 103 that is worn by the user 101 during the sleep session. The time-series sensor data, as it is collected and/or after collection, may be processed to detect sleep-related breathing events. For example, the sensor data may be processed along a rolling window to generate feature values for a plurality of features. Any number of features may be defined and utilized to detect sleep-related breathing events. For example, features may include, but are not limited to, a fall in SpO2 by at least x % over a span of y seconds during the rolling time window (this may be for different x and/or y values), a rise in SpO2 by at least x % over a span of y seconds (this may be from different x and/or y values), a sleep stage transition (for example, from a rapid eye movement ("REM") sleep stage to either light sleep stage or an awake sleep stage), an SpO2 fall by at least x % followed within m seconds by a y % rise in SpO2, all within s seconds of a rise of at least r beats per minute ("bpm") of the heart rate (this may be for different x, y, s and/or r values), wearable device accelerometer activity exceeding x % of a baseline during sleep stage, etc. As will be appreciated, any number and/or type of features may be defined in accordance with the disclosed implementations that are useful in detecting sleep-related breathing events.

Two or more of the feature values may be combined to generate a combined feature value and a determination made, based at least in part on the combined feature value, as to whether the combined feature value is indicative of a sleep-related breathing event. For example, and as discussed further below, two or more feature values of features during a rolling window of the time-series data may be combined to generate a combined feature value and if that combined feature value exceeds a threshold, it may be determined that the sensor data utilized to generate the feature values for the combined feature value is indicative of a sleep-related breathing event.

Finally, upon determination of one or more sleep-related breathing events, a presentation that is explanatory of the determined sleep-related breathing event may be generated and presented, for example to the user. As illustrated in FIG. 1, a graph 108 indicating different combined feature values determined during a sleep session that have been determined as indicative of sleep-related breathing events may be generated and presented on a device 102 along with additional explanations such as a sleep session score 106 and/or a duration of the presented analysis 104. Such information may be beneficial to the user and/or others in determining potential sleep disorders. For example, based on the determined sleep-related breathing events for the user 101 during a sleep session, as illustrated by the graph 108, it is determined that the user's AHI (also referred to herein as a sleep session score) is moderate, which is indicative of between fifteen and thirty sleep-related breathing events per hour. Additional explanations 104 may also be presented to provide a basis as to how and during which time frame the information was determined. Likewise, an AHI as a sleep session score is provided only as an example and other indexes or scores may likewise or alternatively be utilized as a sleep session score.

As discussed further below, a sleep-related breathing event detection model may be generated that processes sensor data to determine feature values, combined feature values, and/or to determine potential sleep-related breathing events based off those combined feature values. The detection model may be based on a learning algorithm that includes feature generation and regression.

In some implementations, sensor data and determination of sleep-related breathing events may be performed entirely on the wearable device such that collected data is never transmitted from the wearable device. In such an example, the explanatory information or graph indicative of determined sleep-related breathing events may be presented on the wearable device, and/or transmitted to another device for presentation, such as a mobile device of the user. Alternatively, some or all of the sensor data may be sent to one or more remote computing resources for computation and determination of potential sleep-related breathing events.

Figure 2:
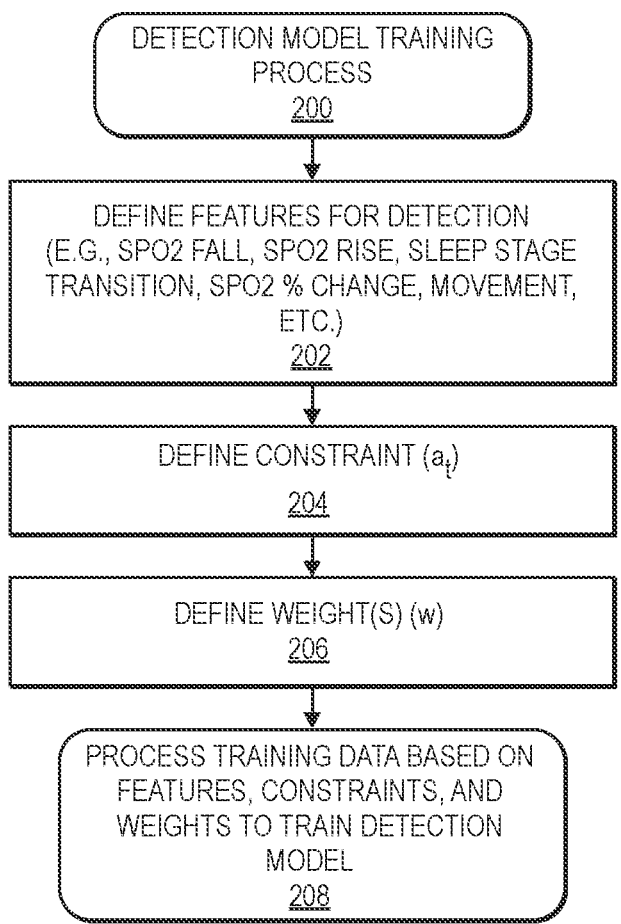
FIG. 2 is an example detection model training process, in accordance with described implementations.

FIG. 2 is an example detection model training process 200, in accordance with described implementations.

The example process 200 begins by defining a plurality of features for detection during a sleep session, as in 202. A feature ("f"), as described herein, may be a function of a small window of time-series sensor data received from one or more sensors of the wearable device which is thought to possibly correlate with a sleep-related breathing event, such as apnea. Features may be directly determined and/or determined based on processing of sensor data that is correlated with sleep-related breathing events. As noted above, features may include, but are not limited to, a fall in SpO2 by at least x % over a span of y seconds during the rolling time window (this may be for different x and/or y values), a rise in SpO2 by at least x % over a span of y seconds (this may be from different x and/or y values), a sleep stage transition (for example, from a rapid eye movement ("REM") sleep stage to either light sleep stage or an awake sleep stage), an SpO2 fall by at least x % followed within m seconds by a y % rise in SpO2, all within s seconds of a rise of at least r beats per minute ("bpm") of the heart rate (this may be for different x, y, s and/or r values), wearable device accelerometer activity exceeding x % of a baseline during sleep stage, etc. A set of two or more features is referenced herein as $\mathcal{F}$.

For each feature $f \in \mathcal{F}$ and for each second t in the time-series data collected during sleep session, a value of $f_t$ may be computed for a rolling time window ending at the time t. Each $f_t$ may be partially indicative as to whether the user is experiencing a sleep-related breathing event at time t. When combined, as discussed herein, the combined value may be conclusively indicative of a sleep-related breathing event.

Figure 5:
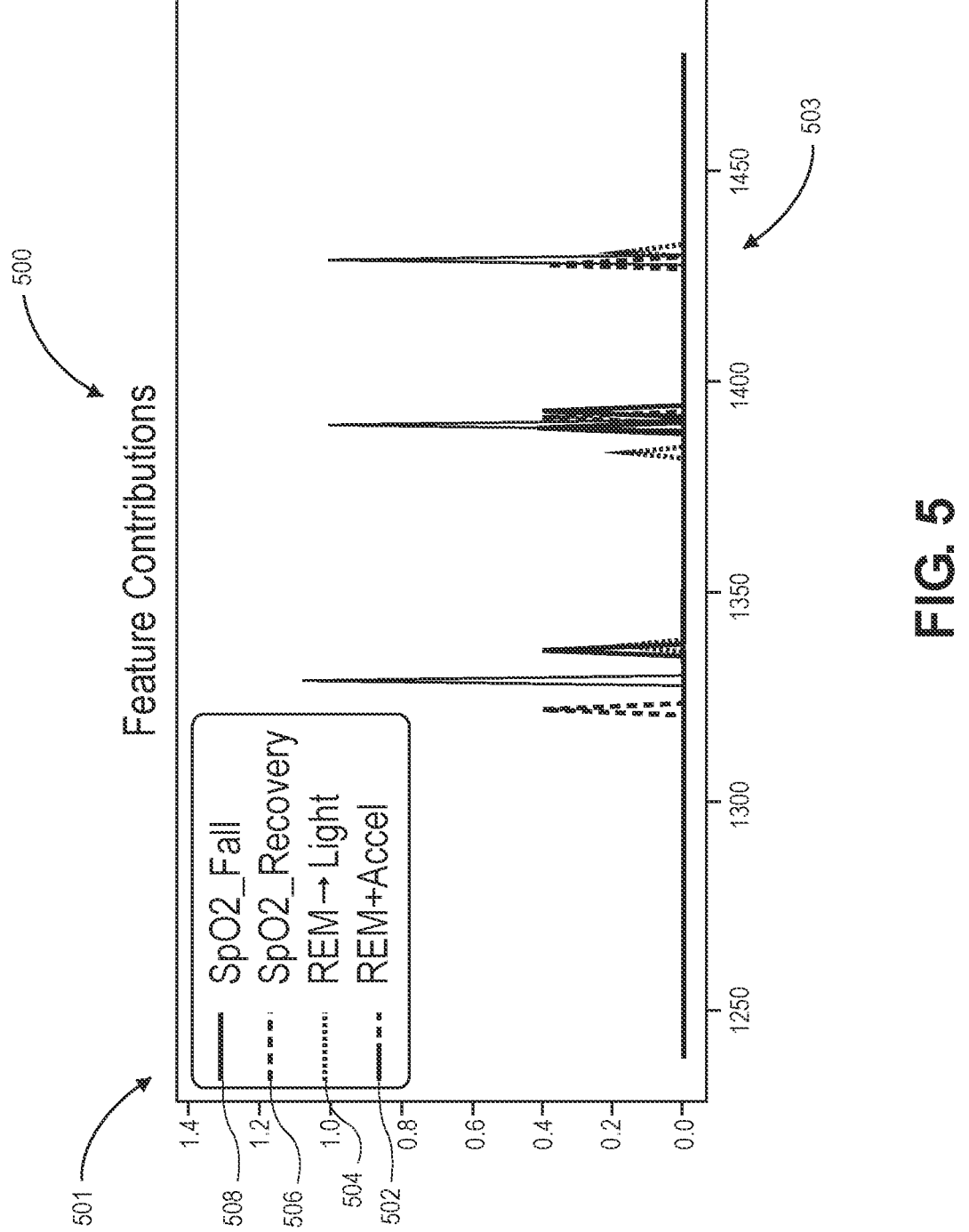
FIG. 5 is an example graph illustrating feature values indicative of sleep-related breathing events determined from different sensor data of a wearable device, in accordance with described implementations.

For example, FIG. 5 is an example graph 500 illustrating feature values indicative of sleep-related breathing events determined from different sensor data of a wearable device, in accordance with described implementations. As illustrated, the example graph 500, indicates determined feature values for different features, such as an SpO2_Fall 508, SpO2_Recovery 506, a transition from a REM sleep stage to light sleep stage 504, and a REM sleep stage in addition to accelerometer activity feature 502. As indicated, the graph 500 presents the determined feature values for each of the features 502, 504, 506, 508 during a rolling time window of the sleep session along the horizontal axis indicative of time 503. Likewise, the value of 501 is presented along the vertical axis to indicate the computed feature value for the features 502, 504, 506, 508.

Because the precise placement of a sleep-related breathing event is unknown and because different features may occur at different points over the time-series data corresponding to a sleep-related breathing event, a real-valued time-series $\{a_t\}$ satisfying $\Sigma_t a_t \approx \Sigma_t \hat{a}_t$ is determined so that multiple features and corresponding feature values, each of which may be partially indicative of a sleep-related breathing event, may be combined to collectively account for a single sleep-related breathing event.

In some implementations, a constraint may be defined, as in 204, along with one or more weights, as in 206. For example, a constraint may be defined requiring that $a_t$ be a linear combination of the $\{f_t\}$ s so that for some weight vector w each $\hat{a}_t$ can be represented as $\hat{a}_t \approx \Sigma_{f \in \mathcal{F}} w_f f_t$ so that the target becomes:

$$\sum_t a_t \approx \sum_t \hat{a}_t = \sum_t \sum_{f \in \mathcal{F}} w_f f_t = \sum_{f \in \mathcal{F}} \sum_t w_f f_t = \sum_{f \in \mathcal{F}} w_f \sum_t f_t$$

Learning a weighting vector w for the above objective function only depends on knowing the total value of $\Sigma_t f_t$ s rather than on individual terms of $f_t$. Accordingly, as long as the $\Sigma_t f_t$ s are precomputed, the dimensionality of the learning problem does not depend on the length of the time-series data of a sleep session (which is usually 20,000-30,000). Because the dimensionality of the learning problem does not depend on the length of the time-series data, more computationally intensive machine learning algorithms may be used to define a weighting vector because there is less data that needs to be processed. Likewise, the trained detection model is both explainable and lightweight enough to store on a wearable device. In some implementations, during training, a machine learning model may further define features based on patterns of training data and labels.

In addition, for sleep-related breathing events for which explanations are not needed, only one value for each $f \in \mathcal{F}$ needs to be stored on the wearable device. For example, only an aggregate total value over an entire sleep session needs to be stored for each $f \in \mathcal{F}$. For sleep-related breathing events for which explanations are to be presented, sensor data from regions of interest, such as those where $\Sigma_{t \in T} f_t$, in which T is a rolling window during a sleep session is large may be recorded in a memory of the wearable device and/or transmitted to another device. The determined feature values can then be easily recomputed on the recorded data. In addition, because the detection model can be used in a streaming manner, outputs generated in accordance with the disclosed implementations (e.g. indications of sleep-related breathing events) may be used to control or send signals to assistive breathing devices, smart beds (e.g., to adjust the incline of the mattress), or other tools used to help manage sleep disorders during a user sleep session.

In some implementations, the weight w may be determined as a two-step process. For example, the Pearson correlation of each feature may be independently determined based on the various labels included in the training data and features of low importance may be discarded or their weight set to zero. Discarding or setting the weight to zero of low interest features ensures that each feature can be independently interpreted in the final output and further limits the required search space. As a second step, a regression model, such as a non-negative LASSO regression, may be used to determine the weight w. Such a regression model may be used to find the sparse linear combinations that best approximate sleep-related breathing events, which is helpful for presenting explanations and generalization. Utilizing non-negativity ensures that the directionality of the weight w is correct.

The detection model may then be trained by processing training data utilizing the features, constraints, and weights, as in 208. For example, a set of labeled training data that includes sensor data collected during a sleep session, for which sleep-related breathing events occurring during that sleep session have been labeled, may be utilized to train the detection model. Training may include, but is not limited to, processing the sensor data to generate feature values for the defined features in accordance with the constraints and corresponding weights. Two or more the feature values may then be combined along a sliding window to generate a combined feature value which may be indicative of a sleep-related breathing event. Likewise, in some implementations, two or more combined feature values may be further combined as indicative of a sleep-related breathing event. Such training, may include, determining which features and corresponding feature values are more indicative of sleep-related breathing events, along with determining the arrangement of features and corresponding feature values that may be indicative of sleep-related breathing events.

Figure 4:
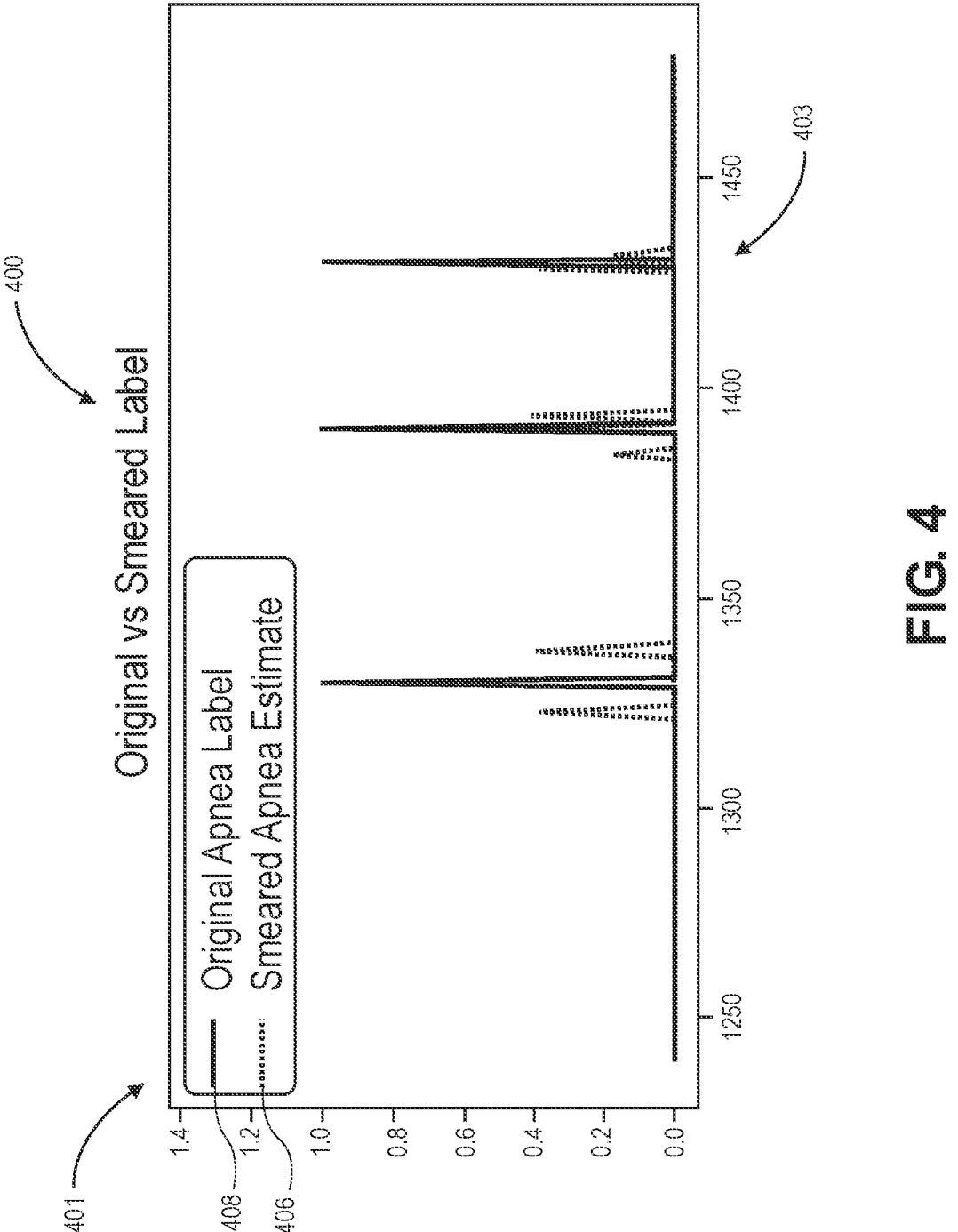
FIG. 4 is an example graph illustrating the comparison between known sleep-related breathing events and detected sleep-related breathing events, in accordance with described implementations.

For example, referring to FIG. 4, illustrated is an example graph showing the comparison between known sleep-related breathing events 408 and detected sleep-related breathing events represented as combined feature values 406, in accordance with described implementations. For example, known sleep-related breathing events 408 may be determined from laboratory monitored sleep studies, as is traditionally done. Likewise, wearable device sensor data collected during such a laboratory monitored sleep study may be processed to determine feature values and corresponding combined feature values 406. As illustrated, determined combined feature values 406 are aligned in time with the occurrence of the known sleep-related breathing events 408. Accordingly, using the labeled training data, such as that illustrated in the graph 400, the detection model may be trained to determine sleep-related breathing events based on feature values computed from sensor data of a wearable device worn by a user during a sleep session.

In some implementations, robustness may be added to model training by perturbing some or all of the labeled training data to indicate noisy samples from a realistic noise profile. For example, a labeled SpO2 signal may be perturbed to improve robustness as SpO2 is often a noisy signal when received from a wearable device.

With a trained detection model, as discussed further below; sleep-related breathing events can be detected based on sensor data from a wearable device during a sleep session of a user and intelligible information presented, for example to the user, explaining the detected sleep-related breathing events and any potential sleep-related disorders, such as an apnea or hypopnea.

Figure 3:
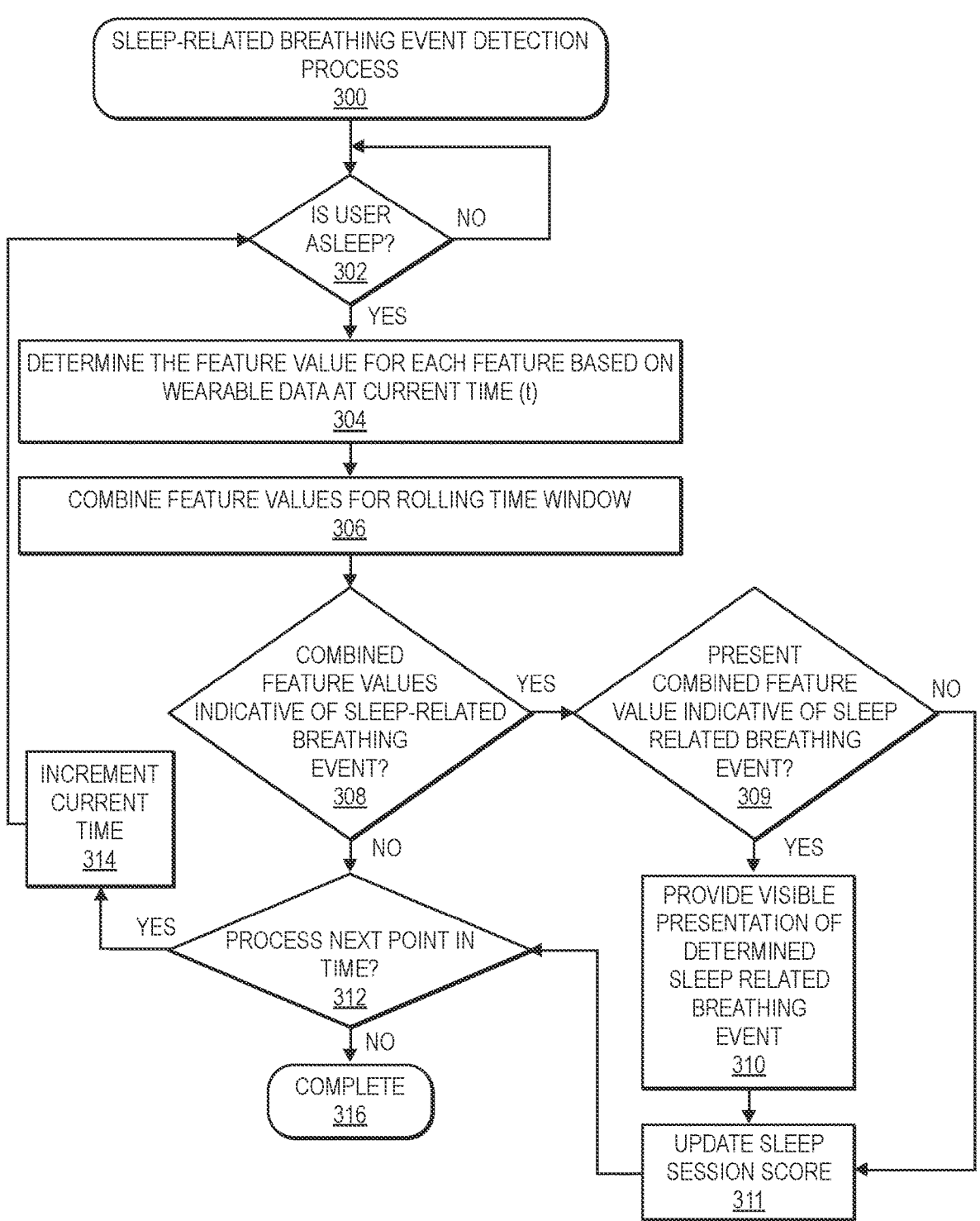
FIG. 3 is an example sleep-related breathing event detection process, in accordance with described implementations.

FIG. 3 is an example sleep-related breathing event detection process 300, in accordance with described implementations.

The example process 300 begins by determining if the user is in a sleep state, as in 302. For example, in some implementations, sensor data from a wearable device worn by user may be processed to determine if the user is in a sleep state, such as a REM sleep state, a light sleep state, a deep sleep state, etc. Additional details for determining if a user is in a sleep state may be found in co-pending U.S. patent application Ser. No. 17/171,821, filed Feb. 9, 2021, and titled "Predicting Sleep Stages of a Sleep Session," the contents of which are herein incorporated by reference in their entirety.

If it is determined that the user is not in a sleep state, the example process 300 returns to block 302 and continues. However, if it is determined that the user is a sleep state, feature values for each of a plurality of features may be determined based on sensor data collected at a current point in time or during a rolling time window as the sensor data is received from sensors of the wearable device, as in 304.

As feature values are determined, two or more of the feature values may be combined during a rolling time window to generate a combined feature value, as in 306. For example, if different feature values are determined from sensor data received during a rolling time window of a sleep session, also referred to herein as time-series data, those different feature values may be combined as fractional values which may collectively be indicative of a sleep-related breathing event.

A determination may then be made as to whether the combined feature value is indicative of a sleep-related breathing event, as in 308. In some implementations, the trained detection model may output a probability or other indication indicative of a confidence as to whether the combined feature value is indicative of the sleep-related breathing event. As another example, a threshold may be defined and if the combined feature value exceeds the threshold, it may be determined that the combination of feature values that constitute the combined feature value are indicative of a sleep-related breathing event.

If it is determined that the combined feature value is indicative of a sleep-related breathing event, a determination may be made as to whether the combined feature value is to be visibly presented for explanation, as in 309. In some implementations, even though the combined feature value may be determined to be indicative of a sleep related breathing event, only those with a confidence value above a presentation threshold may be presented for visible explanation. This may be beneficial to ease in explanation and understanding of presentations.

Figure 6:
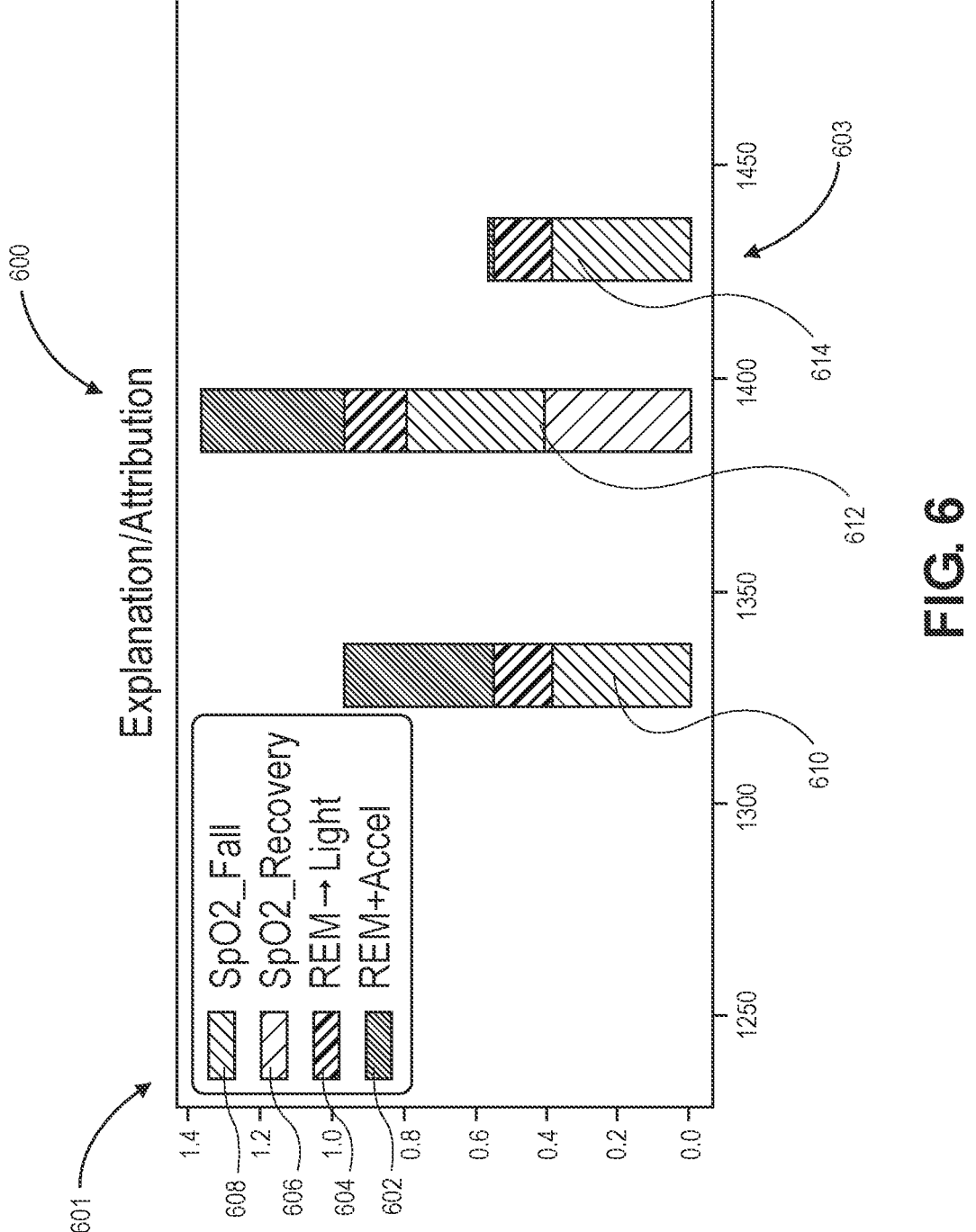
FIG. 6 is an example presentation explaining the basis for determining sleep-related events based on sensor data of a wearable device, and accordance with described implementations.

If it is determined that the combined feature value is to be visibly presented for explanation, a visible presentation explaining the determined sleep-related breathing event may be generated and sent for presentation, for example, to a user via a portable device. For example, FIG. 6 is a graph 600 indicating different combined feature values 610, 612, 614 generated during a time duration 603 of a sleep session of the user. In this example, the different feature values for different features 602, 604, 606, 608 utilized to compute each combined feature value 610, 612, 614 may be graphically illustrated to show the value of each detected feature that was used to generate the combined feature value. For example, feature values of features SpO2_Fall 608, SpO2_Recovery 606, transition between a REM sleep state and a light sleep state 604, and the feature of REM sleep state plus accelerometer movement 602 may be visually presented to illustrate the feature value computed for each such feature in each of the combined feature values 610, 612, 614. The graph 600 may be useful for explanatory purposes, showing how each feature and corresponding feature value contributed to the determination of a sleep-related breathing event during a sleep session of the user. The graph 600 may be presented to the user, a health care provider of the user, or any other person or entity selected by the user.

Returning to FIG. 3, after providing for presentation an indication of the sleep-related breathing event at block 310 or if it is determined at decision block 309 that the combined feature value indicative of the sleep related breathing event is not to be presented, the sleep session score for the sleep session is updated to consider the detection of the sleep related breathing event, such as an AHI for the sleep session, as in 311.

After updating the sleep session score at block 311, or if it is determined that the combined feature value is not indicative of a sleep related breathing event at decision block 308, a determination may be made as to whether a next point in time or rolling time window of the sleep session is to be processed, as in 312. If it is determined that a next point in time/time window is to be processed, the current time is incremented, as in 314, and the example process 300 returns to decision block 302 and continues. If it is determined that the next point in time/time window is not to be processed, for example, the user is no longer in sleep state, the example process 300 completes, as in 316.

Figure 7:
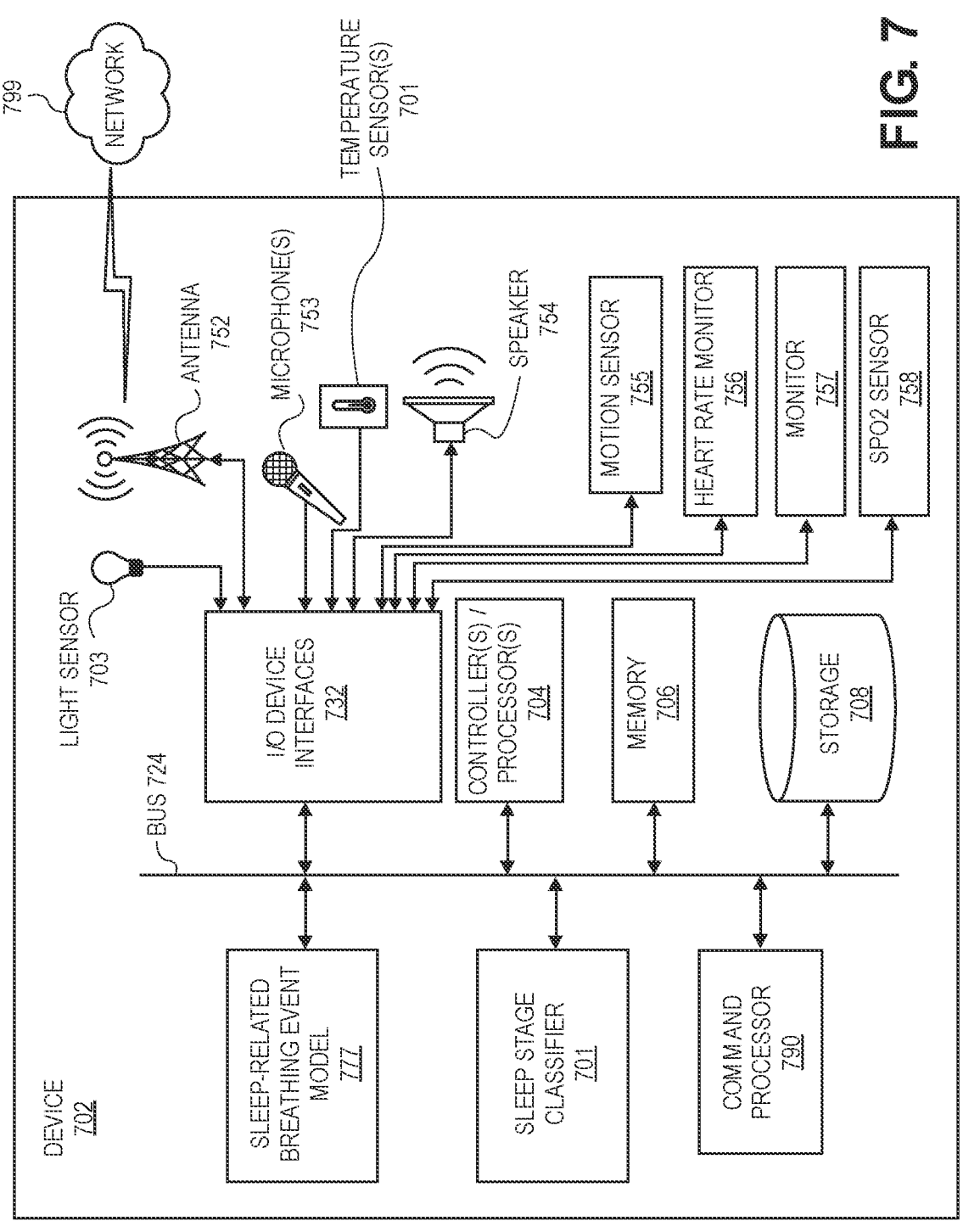
FIG. 7 illustrates example components of a wearable device, in accordance with described implementations.
Figure 8:
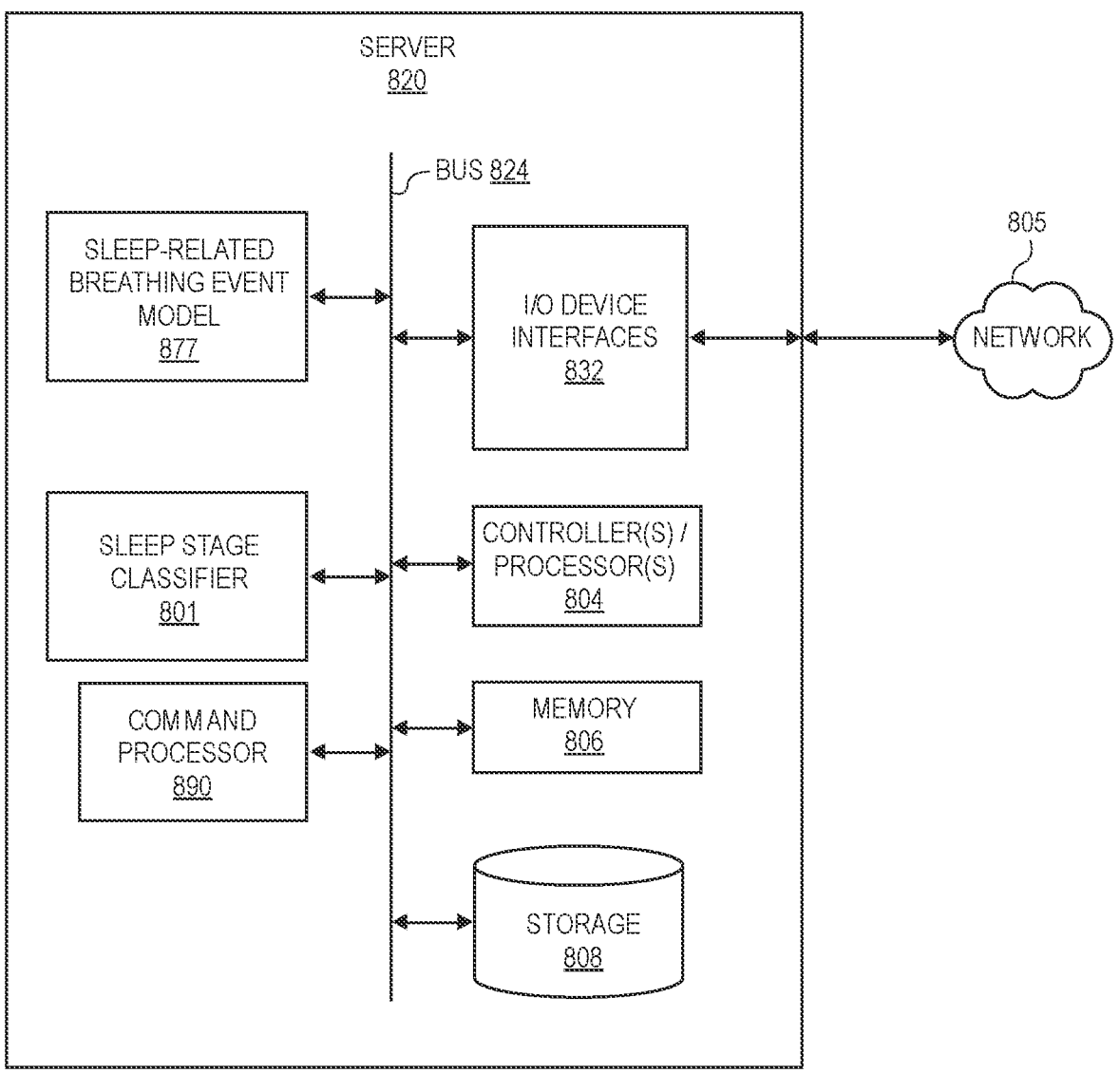
FIG. 8 illustrates example components of a server, in accordance with described implementations.

FIG. 7 is a block diagram conceptually illustrating a wearable device 702 that may be used with the described implementations. FIG. 8 is a block diagram conceptually illustrating example components of a remote computing device, such as a remote server 820 that may be used with the described implementations. Multiple such servers 820 may be included in the system. Alternatively, as discussed above, in some implementations all processing may be done on the wearable device 702. In operation, each of these devices (or groups of devices) may include computer-readable and computer-executable instructions that reside on the respective device (702/820), as will be discussed further below.

Each of these devices (702/820) may include one or more controllers/processors (704/804), that may each include a central processing unit (CPU) for processing data and computer-readable instructions, and a memory (706/806) for storing data and instructions of the respective device. The memories (706/806) may individually include volatile random-access memory (RAM), non-volatile read only memory (ROM), non-volatile magnetoresistive random-access memory (MRAM) and/or other types of memory. Each device may also include a data storage component (708/808), for storing data, controller/processor-executable instructions, features, feature values, combined feature values, etc. Each data storage component (708/808) may individually include one or more non-volatile storage types such as magnetic storage, optical storage, solid-state storage, etc. Each device may also be connected to removable or external non-volatile memory and/or storage (such as a removable memory card, memory key drive, networked storage, etc.) through respective input/output device interfaces (732/832).

Computer instructions for operating each device (702/820) and its various components may be executed by the respective device's controller(s)/processor(s) (704/804), using the memory (706/806) as temporary "working" storage at runtime. A device's computer instructions may be stored in a non-transitory manner in non-volatile memory (706/806), storage (708/808), or an external device(s). Alternatively, some or all of the executable instructions may be embedded in hardware or firmware on the respective device in addition to or instead of software.

Each device (702/820) includes input/output device interfaces (732/832). A variety of components may be connected through the input/output device interfaces. Additionally, each device (702/820) may include an address/data bus (724/824) for conveying data among components of the respective device. Each component within a device (702/820) may also be directly connected to other components in addition to (or instead of) being connected to other components across the bus (724/824).

Referring to the device 702 of FIG. 7, the device 702 may be "headless" and may primarily rely on spoken commands for input and/or through interaction with one or more control interfaces or buttons. In other examples, the device 702 may include a display, which may allow a touch-based interface. The device 702 may also include input/output device interfaces 732 that connect to a variety of components such as an audio output component such as a speaker 754, a wired headset or a wireless headset, and/or other components capable of outputting audio. The device 702 may also include an audio capture component. The audio capture component may be, for example, a microphone 753 or array of microphones, a wired headset or a wireless headset, etc. The microphone 753 may be configured to capture audio, such as environmental noises. If an array of microphones is included, approximate distance to a sound's point of origin may be determined using, for example, acoustic localization based on time and amplitude differences between sounds captured by different microphones of the array.

The device 702 may also include other sensors that collect sensor data. Any number and/type of sensors may be included in the device. In the illustrated example, in addition to the microphone, the device 702 includes a light sensor 703 that may measure the ambient light, one or more temperature sensors 701 that may measure the ambient temperature and/or measure the temperature of the user. In addition, the device 702 may include a motion sensor 755, such as an accelerometer, gyroscope, etc., to measure movement of the user, a heart rate monitor 756 to measure the heart rate of the user, an SpO2 sensor 758 to measure the saturation percentage of oxygen in the blood, and/or other sensors/monitors 757 to measure other user data and/or environment data.

The device may also include a communication interface, such as an antenna 752. Any form of wired and/or wireless communication may be utilized to facilitate communication between the device 702 and other devices. For example, any one or more of 802.15.4 (ZIGBEE), 802.11 (WI-FI), 802.16 (WiMAX), BLUETOOTH, Z-WAVE, near field communication ("NFC"), etc., may be used to communicate between the device 702 and one or more sensors and/or appliances. For example, via the antenna(s) 752, the input/output device interfaces 732 may connect to one or more networks 799/805 via a wireless local area network (WLAN) (such as Wi-Fi) radio, Bluetooth, and/or wireless network radio, such as a radio capable of communication with a wireless communication network such as a Long-Term Evolution (LTE) network, WiMAX network, 3G network, etc. A wired connection such as Ethernet may also be supported.

The device 702 and/or server 820 may also include a command processor (790/890) that is configured to execute commands/functions such as determining feature values, determining combined feature values, along with any presentations and/or explanations indicative of sleep-related breathing events, etc.

The device 702 and/or server 820 may also include one or more machine learning models 777/877. The machine learning model(s) 777/877 may process sensor data collected from sensors of a wearable device worn by, upon, or otherwise in contact with a user during a sleep session to determine potential sleep-related breathing events, as discussed herein. Likewise, the device 702 and/or server 820 may also include a sleep stage classifier 701/801 that is utilized to determine the sleep stage of the user.

In some implementations, multiple devices may be employed in a single system to determine potential sleep-related breathing events during a sleep session, in accordance with the disclosed limitations. The components of the devices 702 and server 820, as illustrated in FIGS. 7 and 8, are exemplary, and may be a stand-alone device or may be included, in whole or in part, as a component of a larger device or system.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers, communications, etc., should recognize that components and process steps described herein may be interchangeable with other components or steps, or combinations of components or steps, and still achieve the benefits and advantages of the present disclosure. Moreover, it should be apparent to one skilled in the art that the disclosure may be practiced without some, or all of the specific details and steps disclosed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage media may be implemented by a volatile computer memory, non-volatile computer memory, hard drive, solid-state memory, flash drive, removable disk and/or other media. In addition, components of one or more of the modules and engines may be implemented in firmware or hardware.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
determining that a user is in a sleep state;
while the user is in the sleep state, receiving from a wearable device worn by the user, a plurality of sensor data collected by a plurality of sensors of the wearable device during a plurality of time series, wherein each time series of the plurality of time series includes a plurality of points in time that occur while the user is in the sleep state;
for a time series of the plurality of time series and based at least in part on sensor data collected during the time series, determining a feature value for each of a plurality of features;
combining two or more of the feature values to generate a combined feature value for the time series;
determining that the combined feature value is indicative of a sleep-related breathing event occurring while the user is in the sleep state; and
in response to determining that the combined feature value is indicative of the sleep-related breathing event, providing a visible presentation of information regarding the sleep-related breathing event,
wherein the information comprises the combined feature value or at least one of the two or more of the feature values, and
wherein the visible presentation is provided on a display of at least one of:
the wearable device; or
a computer device in communication with the wearable device.

2. The computer-implemented method of claim 1, wherein the plurality of features include one or more of a fall in SpO2 by at least a first amount, a rise in SpO2 by at least a second amount, a sleep stage transition from a first sleep stage to a second sleep stage, a fall in SpO2 by at least a third amount followed within a first defined number of seconds by a rise in SpO2 by at least a fourth amount, a change in a heart rate, a sleep stage transition from a third sleep stage followed within a second defined number of seconds by a fall in SpO2 by at least a fifth defined amount, or an accelerometer activity.

3. The computer-implemented method of claim 1, wherein the sensor data includes one or more of a heart rate sensor data, an SpO2 sensor data, a sleep stage classification, a temperature sensor data, an accelerometer sensor data, or an audio data.

4. The computer-implemented method of claim 1, wherein the sleep-related breathing event is at least one of an apnea or a hypopnea.

5. The method of claim 1, wherein the wearable device is at least one of a wrist band, an armband, a neck band, a headband, a ring, a necklace, a sheet, a mattress, a box spring, a pillow, or a clothing.

6. A computing system, comprising:
one or more processors; and
a memory storing program instructions that, when executed by the one or more processors, cause the one or more processors to at least:
receive, during a sleep session of a user, sensor data collected from a plurality of sensors of a wearable device of the user, wherein the sensor data comprises time-series data collected during a window of time;
process the sensor data to generate a plurality of feature values for each of a plurality of features during the window of time;
combine two or more of the feature values to generate a combined feature value;
determine, based at least in part on the combined feature value, that the user has experienced a sleep-related breathing event during the window of time; and
send, for presentation, an indication of the sleep-related breathing event.

7. The computing system of claim 6, wherein the sleep-related breathing event is at least one of an apnea or a hypopnea.

8. The computing system of claim 6, wherein the plurality of features include one or more of a fall in SpO2 by at least a first amount during the window of time, a rise in SpO2 by at least a second amount during the window of time, a sleep stage transition from a first sleep stage to a second sleep stage during the window of time, a fall in SpO2 by at least a third amount during the window of time followed within a first defined number of seconds by a rise in SpO2 by at least a fourth amount during the window of time, a change in a heart rate during the window of time, a sleep stage transition from a third sleep stage followed within a second defined number of seconds by a fall in SpO2 by at least a fifth defined amount during the window of time, or an accelerometer activity during the window of time.

9. The computing system of claim 8, wherein the presentation comprises a display of at least one of the two or more of the feature values by at least one of:
the computing system; or
the wearable device.

10. The computing system of claim 6, wherein the sensor data includes one or more of a heart rate sensor data, an SpO2 sensor data, a sleep stage classification, a temperature sensor data, or an accelerometer sensor data.

11. The computing system of claim 6, wherein a duration of the window of time is less than a duration of the sleep session.

12. The computing system of claim 6, wherein the program instructions, when executed by the one or more processors to determine that the user has experienced the sleep-related breathing event, further cause the one or more processors to at least:
apply a weighting value to at least one of the two or more of the feature values; and
wherein the combined feature value is generated, with the weighting value applied to the at least one of the two or more of the feature values.

13. The computing system of claim 6, wherein the program instructions that, when executed by the one or more processors to determine that the user has experienced the sleep-related breathing event, further cause the one or more processors to at least:
process the combined feature value using a detection model to determine that the user has experienced the sleep-related breathing event.

14. The computing system of claim 13, wherein the detection model is trained to consider feature values determined based on sensor data collected during a window of time and an arrangement of those feature values during the window of time to determine that the user has experienced the sleep-related breathing event.

15. The computing system of claim 6, wherein the wearable device is at least one of a wrist band, an armband, a neck band, a headband, a ring, a necklace, a sheet, a mattress, a box spring, a pillow, or a clothing.

16. A method, comprising:
processing sensor data collected from a plurality of sensors of a wearable device worn by a user during a sleep session to determine a plurality of feature values, wherein each one of the plurality of feature values is determined for one of a plurality of features;
combining two or more of the plurality of feature values determined during a window of time of the sleep session to generate a combined feature value;
determining, based at least in part on the combined feature value, that the user has experienced a sleep-related breathing event during at least the window of time; and
sending, for presentation, an indication of the sleep-related breathing event during at least the window of time and at least one of the two or more of the plurality of feature values,
wherein the presentation includes a display of at least the indication and the at least one of the two or more of the feature values determined during the window of time by at least one of:
the wearable device; or
a computing system in communication with the wearable device.

17. The method of claim 16, further comprising:
determining, during the sleep session and based at least in part on the sensor data, a plurality of sleep-related breathing events experienced by the user during the sleep session,
wherein the presentation further includes a display of an indication of a severity of a sleep disorder by the at least one of the wearable device or the computer system in communication with the wearable device, and
wherein the severity is determined based at least in part on the plurality of sleep-related breathing events.

18. The method of claim 17, wherein the sleep disorder is at least one of an apnea or a hypopnea, and
wherein the severity is determined in accordance with an Apnea-Hypopnea Index ("AHI").

19. The method of claim 16, wherein the plurality of features include one or more of a fall in SpO2 by at least a first amount during the window of time, a rise in SpO2 by at least a second amount during the window of time, a sleep stage transition from a first sleep stage to a second sleep stage during the window of time, a fall in SpO2 by at least a third amount during the window of time followed within a first defined number of seconds by a rise in SpO2 by at least a fourth amount during the window of time, a change in a heart rate during the window of time, a sleep stage transition from a third sleep stage followed within a second defined number of seconds by a fall in SpO2 by at least a fifth defined amount during the window of time, or an accelerometer activity during the window of time.

20. The method of claim 16, wherein the wearable device is at least one of a wrist band, an armband, a neck band, a headband, a ring, a necklace, a sheet, a mattress, a box spring, a pillow, or a clothing, and wherein the sensor data includes one or more of a heart rate sensor data, an SpO2 sensor data, a sleep stage classification, a temperature sensor data, or an accelerometer sensor data.

\* \* \* \* \*